United States Patent [19]
Rothe et al.

[11] 3,979,520
[45] Sept. 7, 1976

[54] PREPARATION OF RAPIDLY RESORBABLE GLIBENCLAMIDE

[75] Inventors: Werner Rothe, Hockenheim; Helmut Heinemann, Heidelberg; Felix Helmut Schmidt, Mannheim-Seckenheim; Günter Betzien, Mannheim, all of Germany

[73] Assignee: Boehringer Mannheim G.m.b.H., Mannheim, Germany

[22] Filed: Sept. 20, 1974

[21] Appl. No.: 508,001

[30] Foreign Application Priority Data
Sept. 26, 1973 Germany............................. 2348334

[52] U.S. Cl. ................................................ 424/321
[51] Int. Cl.² ........................................ A61K 31/17
[58] Field of Search ................................... 424/321

[56] References Cited
UNITED STATES PATENTS
3,507,954  4/1970  Weber et al. ...................... 424/321

OTHER PUBLICATIONS

Remington's – Pharmaceutical Sciences – 13th ed., – J. Hoover – Hack Publ. Co., Easton, Pa. 1965, pp. 195–197, 332–333 and 420.

*Primary Examiner*—V. D. Turner
*Assistant Examiner*—D. W. Robinson
*Attorney, Agent, or Firm*—Burgess, Dinklage & Sprung

[57] ABSTRACT

Rapidly resorbable particulate glibenclamide having a particle surface area of active material of at least 3 m²/g is produced by precipitating the active material from its solution in an organic solvent or in water or aqueous alcohol, preferably rendered alkaline, using water which is preferably acidified.

5 Claims, 1 Drawing Figure

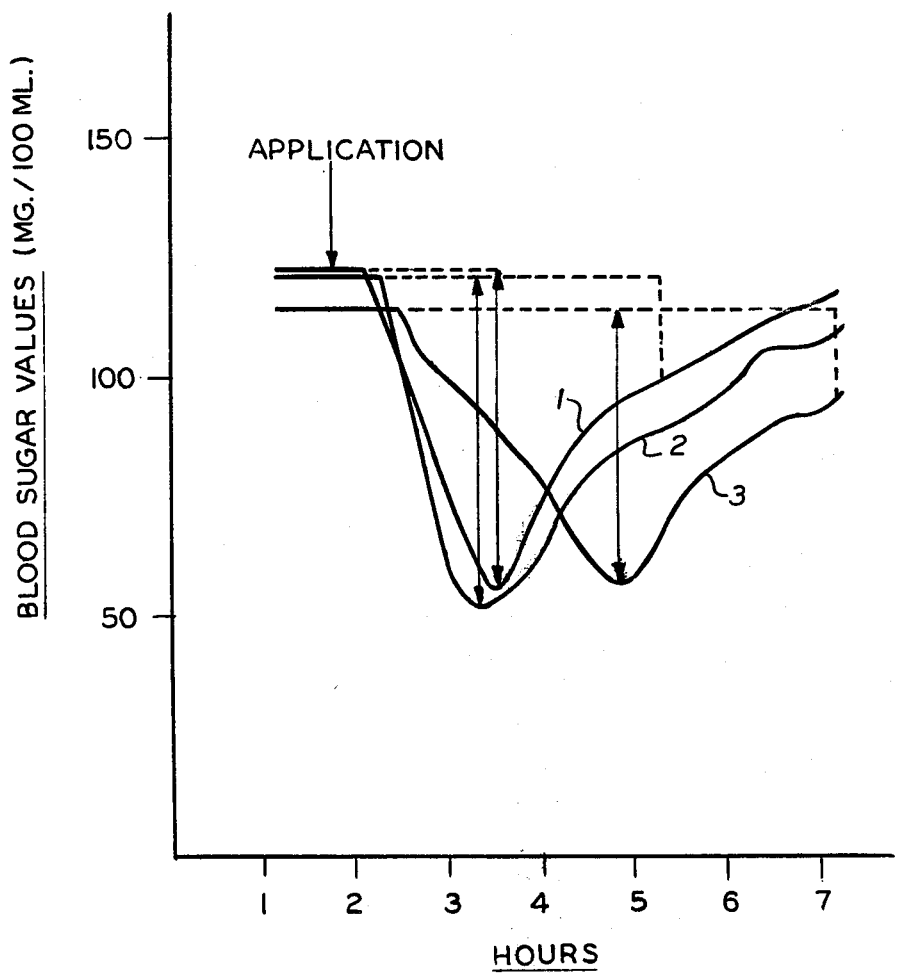

PREPARATION OF RAPIDLY RESORBABLE GLIBENCLAMIDE

The present invention is concerned with a new form of N-4-[2-(5-chloro-2-methoxybenzamido)-ethyl]-phenyl-sulfonyl-N'-cyclohexylurea.

N-4-[2-(5-chloro-2-methoxybenzamido)-ethyl]-phenyl-sulfonyl-N'-cyclohexylurea is a highly effective chemotherapeutic agent which is also known as "glibenclamide" and as "HB 419." It is a recent sulfonylurea derivative with the greatest hitherto known blood sugar lowering action and the lowest degree of side effects so that it is especially suitable for the treatment of diabetes mellitus.

It is known that the therapeutic value of an active material can depend, to a large extent, upon the form of administration and the formulation employed. This also applies to glibenclamide (see W. Rupp, O. Christ and W. Fülberth, Arzneimittel-Forschung (Drug. Res.), 22, 471–473/1972). In particular, a prerequisite for dependable action is resorption of the active material from a pharmaceutical preparation as completely as possible. This prerequisite is fulfilled for the glibenclamide in commercially available preparations. in pharmacokinetic studies, it has been demonstrated that a practically complete intestinal resorption takes place from the commercially available forms (see W. Rupp et al., loc. cit.).

It is generally known that the degree of resorption of sparingly soluble active materials depends upon their degree of division, i.e., particle size. In the commercial preparation, glibenclamide is present in the form of particles with a surface area of 1–2 $m^2/g$. This fine degree of division is the prerequisite for the 100 percent degree of resorption achieved with this preparation.

We have now, surprisingly, found that with the preparations according to the present invention, by increasing the particle surface area to at least 3 $m^2/g$ the complete resorption is retained along with a markedly more rapid lowering of the blood sugar than with the previously known preparations.

The more rapid resorption has two main advantages:
a. since the tablets are administered simultaneously with a meal, the active material passes, together with the carbohydrates, into the organism so that the need for the active material and its supply are synchronized; and
b. in the case of slower resorption, there is the danger that, several hours after administration, significant amounts of active material continue to be resorbed without a corresponding supply of carbohydrates. In this way, hypoglycaemias can occur. This danger is overcome by the more rapid resorption.

It is economically advantageous that the forms of administration according to the present invention can be produced in a technically simple manner by means of working methods which are conventional in the pharmaceutical industry. Thus, we have found that the active material must be present in an especially fine state of division with a particle surface area of at least 3 $m^2/g$ in order to achieve the above-mentioned increase of the blood sugar-lowering action. The fine crystallizate according to the present invention can be worked up to conventional pharmaceutical compositions, for example, tablets, dragees or capsules, by admixture with solid or liquid pharmaceutical diluents or carriers. Each such unit dose contains about 0.5 to 10 mg and preferably about 1 to 5 mg of active material.

For the production of tablets and dragees, which represent the preferred forms of administration for this oral antidiabetic, there can be used all the conventional tablet adjuvants. Although the mechanism of the manner of working of dispersion agents added according to the present invention has still not been fully elucidated, it is to be assumed that dispersion agents prevent an aggregation of the very fine particles of the active material in the alimentary tract and thus assist the resorption thereof. Therefore, according to the present invention, the term "dispersion agent" is to be broadly interpreted and is to be understood to include all materials which prevent a reagglomeration of the finely divided glibenclamide. In the case of administration of the glibenclamide in tablet form, there can already be present substances such as polyglycols, lactose, starch, cellulose and the like, which also function as dispersion agents when they are present in large excess.

However, it has proved to be especially advantageous, as additional dispersion agent, also to incorporate a wetting agent into the tablet mass. Per one part of the glibenclamide, it is sufficient to use about 2 to 100 and preferably about 2 to 20 parts of the wetting agent in order to bring about the resorption requirements according to the present invention, a ratio of about 1:5 to 1:10 being especially preferred. As wetting agent, it has proved to be especially useful to employ polyoxyethylene stearate but other wetting agents can also be used insofar as they are pharmacologically compatible.

The process according to the present invention for the production of a highly effective, completely resorbed form of administration of glibenclamide is characterized in that the glibenclamide is brought to a particle surface area of at least 3 $m^2/g$ by precipitation from a solution or by grinding, followed by mixing with a dispersion agent.

Degrees of division of this order can only be achieved by grinding with very great difficulty. We have found that grinding 3 or 4 times with a jet mill, possibly with the addition of milling adjuvants, just suffices to achieve a particle surface area of 3 $m^2/g$, corresponding to a particle size of about $2\mu$.

The fine crystallizate according to the present invention with a surface area of at least 3 $m^2/g$, and preferably of about 5–10 $m^2/g$, is preferably achieved by precipitation of the glibenclamide from a solvent.

It has proved to be especially useful to dissolve the glibenclamide in a water-miscible organic solvent and to introduce this solution, preferably with intensive mixing, into a weakly acidified aqueous medium. The choice of the solvent is, in itself, not critical; all solvents can be used which dissolve the glibenclamide in sufficient amounts. Preferably there are used lower alcohols, e.g., lower alkanols of up to about 4 carbon atoms, dimethyl formamide or dimethyl sulfoxide.

Since the solubility of glibenclamide in water reaches a minimum at a pH of 4, the aqueous medium is preferably acidified somewhat. As acid, it has proved to be especially useful to employ acetic acid, citric acid, ascorbic acid, or the like.

According to a further variant of the process, either a soluble salt of glibenclamide is directly dissolved in water or in an aqueous alcohol or the glibenclamide is introduced into a calculated amount of an aqueous solution of an alkali metal hydroxide and the solution thus obtained is then introduced into a weakly acidified aqueous medium. A disadvantage of this process has been found to be that, in the case of comparatively large batches, considerable amounts of heat of neutralization must be removed but, on the other hand, the substantially simpler handling of aqueous solutions in comparation with the use of organic solvents is advantageous. In the case of this process, too, ascorbic acid, acetic acid or citric acid is preferably used for the neutralization since with these acids the optimum pH range of about 4 to 7 for the precipitation can be controlled especially easily.

In the synthesis of glibenclamide, there is obtained a pure crystalline product with a particle size of about 50–1000$\mu$ and a melting point of 172°–174°C. For further working up into pharmaceutical compositions, this product is usually ground to a particle size of about 10$\mu$, i.e., a particle surface area of about 1 m$^2$/g and worked up, with the necessary additives, into tablets or dragees. The forms of administration according to the present invention contain the glibenclamide with a particle surface area of at least 3 m$^2$/g, i.e., a particle size of at most 2$\mu$. In this previously unknown degree of division, glibenclamide shows, surprisingly, even a melting point depression or an increase of the melting range. Furthermore, since the substance is absolutely pure, this is to be attributed to the increased surface energy of the small particles.

The preparation of glibenclamide with a surface area, according to the invention, of 3–10 m$^2$/g is illustrated by the following Examples, the surface areas given therein being determined by the BET method (see Brunauer, Emmet and Teller, J.A.C.S., 60, 309-319/1938).

EXAMPLE 1

50 g of glibenclamide are dissolved at 40°–50°C in 116 g of dimethyl formamide. This solution is then run, with intensive stirring, into about 1 liter of cold water. The glibenclamide is thus obtained as a finely divided suspension which is filtered off and copiously washed with water. After drying at 50°C., the yield is 90–95%. The product has a particle surface area of 5.79 m$^2$/g. The melting point is 170.5°–172°C.

EXAMPLE 2

50 g of glibenclamide are dissolved in 100 ml of dimethyl formamide, with gentle warming at 47°C. In a 3 liter tubular vessel there is placed a solution of 20 g of citric acid in 980 ml of water. An Ultra Turrax turbine stirrer (type T 45 N) dips into the solution. While stirring at 5000 rpm, the dimethylformamide solution of glibenclamide is uniformly added, via a dropping funnel, a tube and a thin canula, directly into the suction opening of the stirrer head over the course of 5 minutes. The temperature increases from 20° to 41°C. The suspension obtained thereafter is immediately filtered off with suction. The substance is washed with water and dried at 60°C in a circulating air cabinet. The yield is 48.5 g (97% of theory) and the product has a melting point of 166°–169°C and a particle surface area of 9.8 m$^2$/g.

EXAMPLE 3

50 g of glibenclamide are dissolved in 100 ml of dimethyl formamide, 6 g of glacial acetic acid are dissolved in 1 liter of water in a 3 liter tubular vessel. The experimental procedure is as described in Example 1. In addition, a cooling coil dips into the solution. While stirring at 5000 rpm and cooling with ice water, the dimethyl formamide solution of glibenclamide is introduced into the suction opening of the stirrer head over the course of 2 minutes. The temperature increases from 6° to 13°C. Subsequently, the product is filtered off with suction, washed with water and dried at 60°C. The yield is 46.8 g (97.6% of theory) and the product has a melting point of 170°–172°C and a particle surface area of 6.0 m$^2$/g.

EXAMPLE 4

400 g of glibenclamide are dissolved in 8000 ml of dimethyl formamide at about 50°C (Solution 1). 2750 ml of 2N acetic acid are diluted with 50 liters of water (Solution 2). A solution of 55 ml of 2N acetic acid in 1 liter of water is placed in a 3 liter tubular vessel equipped with a cooling coil and an Ultra Turrax stirrer. While stirring at 5000 rpm, by means of a dosing pump, Solutions 1 and 2 are pumped into the stirrer head at the respective rates of addition of 1 liter per hour and 65 liters per hour. The temperature is 8°C. The volume in the vessel is kept constant by constantly withdrawing the suspension formed from above into a suction flask. Alternatively, an overflow can be used. The suspension is filtered with suction and the product obtained is washed with water and dried at 60°C. The yield is 97% of theory. The product has a melting point of 169.5°–172°C and a particle surface area of 6.8 m$^2$/g.

EXAMPLE 5

100 g of the sodium salt of glibenclamide are dissolved at 35°C in a mixture of 1340 ml of methanol and 176 ml of water, treated with 2.8 g of active charcoal, filtered and the charcoal washed with a mixture of 40 ml of methanol and 6 ml of water. In a 3 liter tubular vessel there is placed a solution of 12 g of glacial acetic acid in 1 liter of water. While stirring at 5000 rpm and cooling with ice water, the methanolic solution is allowed to run in via a dropping funnel and canula into the suction opening of the stirrer head of the stirrer used over the course of 7 minutes. The temperature increases from 9° to 19°C. The suspension is filtered off with suction, washed with water and dried at 60°C. The yield is 94% of theory and the product has a melting point of 164°–168°C and a particle surface area of 10.3 m$^2$/g.

EXAMPLE 6

2.7 kg of glibenclamide are dissolved at about 50°C in 5.4 liters of dimethyl formamide. A solution of 350 ml of glacial acetic acid in 54 liters of water is placed in a 100 liter V4A steel vessel. The solution is cooled by standing the 100 liter V4A steel vessel in a larger vessel filled with ice water. An Ultra Turrax turbine stirrer (type T 115) dips into the acectic acid solution. While stirring at 2300 rpm, the dimethyl formamide solution of glibenclamide is fed by means of a dosing pump at the rate of 13 liters per hour directly into the suction opening of the stirrer head. The temperature increases from 11° to 17°C. The suspension is filtered off with suction or is forced through a filter. The product is washed with water and dried at 60°C. The yield is 97% of theory and the product has a melting point of 172°–173°C and a particle surface area of 5.2 m$^2$/g.

EXAMPLE 7

3 kg of the sodium salt of glibenclamide are dissolved at 35°C in a mixture of 40 liters of methanol and 5.3 liters of water, treated with 85 g of charcoal and filtered. A solution of 380 ml of glacial acetic acid in 30 liters of water are placed in a 100 liter V4A steel vessel cooled with ice water. While stirring at 2300 rpm and cooling with ice water, the filtered methanolic solution of the sodium salt of glibenclamide is dosed directly into the stirrer head at a rate of about 60 liters per hour. The temperature increases from 7° to 22°C.

The suspension is filtered off with suction or is forced through a filter, washed with water and dried at 60°C. The yield is 94% of theory and the product has a melting point of 166°–168°C and a particle surface area of 7.8 m$^2$/g.

EXAMPLE 8

2 kg glibenclamide with a particle size of 5–300 μ are passed three times through a jet mill. The yield is 1.8 kg (90% of theory) and the product has a melting point of 170°–172°C and a particle surface area of 5.8 m$^2$/g.

The administration of oral anti-diabetic substances to fasting healthy subjects leads, as a rule, to a shorter time interval during which the blood sugar level is lowered, since the lower blood glucose concentrations prematurely initiate counter-regulatory processes. Therefore, in testing for activity an attempt is made to achieve, by means of continuous glucose infusion, a blood sugar level which is as constant as possible, of the order of 120 mg/100 ml by continuous infusion of glucose to test subjects. With the continuous administration of glucose, the antidiabetic substance should only reduce the blood sugar concentration to such an extent that the counter-regulation brings about the smallest possible shortening of the blood sugar lowering brought about by the test substance. By the administration of 14 g of glucose per hour to fasting healthy subjects with a body weight of 70 kg, in 20 blank experiments it was possible to achieve, with a glucose infusion for 7.25 hours, a satisfactorily constant blood sugar level of the order of 120 mg/100 ml. The blood sugar controls were carried out after the commencement of the infusion at 15 minute intervals: in all, using the hexokinase method (micromethod), 31 blood sugar determinations (including two blanks before commencement of the infusion) were made per subject.

In the case of the test substance experiments, under otherwise the same experimental conditions, the test preparation in question was administered 1.75 hours after commencement of the glucose infusion. The experiments were ended, in each case, 7.25 hours after commencement of infusion or 5.5 hours after administration of the test substance, a longer period of infusion not being practical.

The following preparations were administered:

1. A suspension of 1.25 mg of glibenclamide, initially dissolved in 10 ml of water in the form of its sodium salt and precipitated with about 1.0 mg of crystalline ascorbic acid.

2. One half of a tablet according to the present invention of oblong shape and consisting of:

| | |
|---|---|
| 1.25 mg | glibenclamide (particle surface area 5.35 m$^2$/g) |
| 10.00 mg | polyoxyethylene stearate |
| 23.75 mg | lactose |
| 5.00 mg | corn starch |
| 25.00 mg | sodium bicarbonate |
| 3.50 mg | highly-dispersed silicic acid |
| 16.00 mg | urea |
| 0.50 mg | magnesium stearate |
| 85.00 mg | |

3. Half of a commercially available tablet consisting of:

| | |
|---|---|
| 2.5 mg | glibenclamide (particle surface area about 1 m$^2$/g) |
| 39.5 mg | lactose |
| 35.25 mg | corn starch |
| 1.50 mg | talc |
| 0.25 mg | magnesium stearate |
| 1.00 mg | highly dispersed silicic acid |
| 80.00 mg | |

The blood sugar values measured over the course of time is shown in FIG. 1 of the accompanying drawings, curves 1, 2 and 3 corresponding to the above-described preparations 1, 2 and 3.

The parameters determined, which are representative for the experiments, are set out in the following Table:

TABLE

| Representative Parameter | | HB 419 - Suspension | HB 419 - Oblong Tablet | Commercial preparation |
|---|---|---|---|---|
| Number of test subjects | | 21 | 19 | 17 |
| dosage | (mg) | 1.25 | 1.25 | 2.5 |
| blood sugar level (before action) | (mg/100 ml) | 122.1 | 123.7 | 116.8 |
| commencement of action | (h) | 2.23 | 2.10 | 2.42 |
| absorption delay | (h) | 0.49 | 0.36 | 0.67 |
| minimum blood sugar | (mg/100 ml) | 53.4 | 57.4 | 59.1 |
| time of minimum blood sugar (before commencement of action) | (h) | 1.10 | 1.45 | 2.43 |
| blood sugar level (end of action) | (mg/100 ml) | 99.2 | 101.6 | 97.6 |
| period of action | (h) | 3.01 | 3.95 | 4.76 |
| area of action | (mg/100 ml·h) | 125.1 | 159.8 | 155.5 |
| rate of increase of the action | (mg/100 ml/h) | 62.6 | 45.9 | 23.7 |

It will be appreciated that the instant specification and examples are set forth by way of illustration and not limitation, and that various modifications and changes may be made without departing from the spirit and scope of the present invention.

What is claimed is:

1. A process for the preparation of a blood sugar-lowering composition comprising dissolving glibenclamide in a water-miscible organic solvent, combining said solution with water to precipitate out the glibenclamide with a surface area of about 3 to 10 $m^2/g$, and combining the precipitated material with about 2 to 100 times its weight of a pharmacologically acceptable dispersion agent.

2. The process of claim 1 wherein the organic solvent is dimethyl formamide, dimethyl sulfoxide or a lower alkanol and the water is acidifed prior to combination with the organic solution.

3. The process of claim 2 wherein the water is acidified with ascorbic acid, acetic acid or citric acid.

4. A process for the preparation of a blood sugar-lowering composition comprising dissolving glibenclamide in alkaline water or aqueous lower alkanol, combining said solution with acidified water to precipitate out the glibenclamide with a surface area of about 3 to 10 $m^2/g$, and combining the precipitated material with about 2 to 100 times its weight of a pharmacologically acceptable dispersion agent.

5. The process of claim 4 wherein the water is acidified with ascorbic acid, acetic acid or citric acid.

* * * * *